United States Patent [19]
Ogino

[11] Patent Number: 5,902,255
[45] Date of Patent: May 11, 1999

[54] HUMAN MONITORING DEVICE

[75] Inventor: Hiroyuki Ogino, Nara, Japan

[73] Assignee: Matsushita Electric Industrial Co., Ltd., Osaka, Japan

[21] Appl. No.: 08/978,161

[22] Filed: Nov. 25, 1997

Related U.S. Application Data

[60] Continuation of application No. 08/581,116, Dec. 29, 1995, Pat. No. 5,724,990, which is a division of application No. 08/224,104, Apr. 6, 1994, Pat. No. 5,479,939, which is a continuation of application No. 07/784,438, Dec. 20, 1991, abandoned.

[30] Foreign Application Priority Data

| Mar. 9, 1990 | [JP] | Japan | 2-58270 |
| Mar. 12, 1990 | [JP] | Japan | 2-60218 |
| May 25, 1990 | [JP] | Japan | 2-135893 |
| Jun. 20, 1990 | [JP] | Japan | 2-161822 |
| Mar. 7, 1991 | [WO] | WIPO | PCT/JP91/307 |

[51] Int. Cl.$^6$ .................................................. A61B 5/00
[52] U.S. Cl. ............................................................ 600/595
[58] Field of Search .................................... 600/483, 484, 600/587, 595; 5/658; 340/573, 575

[56] References Cited

U.S. PATENT DOCUMENTS

| 3,163,856 | 12/1964 | Kirby . |
| 3,803,571 | 4/1974 | Luz . |
| 3,898,981 | 8/1975 | Basham . |
| 3,926,177 | 12/1975 | Hardway, Jr. et al. . |
| 3,996,922 | 12/1976 | Basham . |
| 4,196,425 | 4/1980 | Williams et al. . |
| 4,295,133 | 10/1981 | Vance . |
| 4,320,766 | 3/1982 | Alihanka et al. . |
| 4,474,185 | 10/1984 | Diamond . |
| 4,665,385 | 5/1987 | Henderson . |
| 4,665,926 | 5/1987 | Leuner et al. . |
| 4,735,199 | 4/1988 | DiLullo . |
| 4,757,453 | 7/1988 | Naseff ...................................... 364/415 |
| 4,836,219 | 6/1989 | Hobson et al. . |
| 5,107,219 | 4/1992 | Guern et al. . |
| 5,197,490 | 3/1993 | Steiner et al. . |
| 5,266,807 | 11/1993 | Neiger . |

FOREIGN PATENT DOCUMENTS

| 2 451 186 | 10/1980 | France . |
| 2451186 | 10/1980 | France . |
| 3 133 026 | 10/1983 | Germany . |
| 3 248 179 | 6/1984 | Germany . |
| 3421045 | 12/1985 | Germany . |
| 55-23614 | 6/1980 | Japan . |
| 57-30498 | 6/1982 | Japan . |
| 57-31902 | 7/1982 | Japan . |
| 58-27932 | 6/1983 | Japan . |
| 1-238825 | 11/1988 | Japan . |
| 63-283623 | 11/1988 | Japan . |
| 1-236033 | 9/1989 | Japan . |

*Primary Examiner*—Max Hindenburg
*Attorney, Agent, or Firm*—Pillsbury Madison & Sutro LLP

[57] ABSTRACT

The body movement of a person in a bed or a seat is detected by a piezo-electric element without contacting to the body, and absence or presence in the bed or the seat and rough body movement are judged by detecting the fine body movement propagated by the functioning of heart and breathing of the body, and in case the presence in bed is judged the time measurement operation is started by the timer, and by judging the absence and rough body movement the time measurement is reset. It is judged that the body on the bed or the seat has fallen asleep when the measurement time of the timer exceeds a predetermined set time.

4 Claims, 10 Drawing Sheets ical Field

HUMAN MONITORING DEVICE

PRIOR APPLICATIONS

This is a continuation of appplication Ser. No. 08/581,116 filed Dec. 29, 1995 now U.S. Pat. No. 5,724,900 which is a divisional of application Ser. No. 08/224,104, filed Apr. 6, 1994 now U.S. Pat. No. 5,479,939 which was a continuation of application Ser. No. 07/784,438, filed Dec. 20, 1991 now abandoned which was based on International Application PCT/JP91/00307, filed Mar. 7, 1991 which designated the U.S. and in turn was based on Japanese Applications Hei 2-58270, filed Mar. 9, 1990, Hei 2-60218, filed Mar. 12, 1990, Hei 2-135893, filed May 25, 1990 and Hei 2-161822, filed Jun. 20, 1990, the priority of all which is claimed and the content of all which is hereby incorporated by reference.

BACKGROUND OF THE INVENTION

1. Technical Field

The present invention relates to a human monitoring apparatus for detecting the presence of a human body and for detecting sleep of the body on a bed or a seat.

Conventionally, this type of human monitoring apparatus is what detects, for example, a brain wave and movement of eyeballs of the body and processes the signal waveform detected to judge falling asleep (Japanese unexamined published Patent Application No. 62-253034 (1987), or detects a pulse wave of the body and processes the signal waveform to judge falling asleep (Japanese unexamined published Patent Application No. Sho 63-150047 (1988)), which are both constituted of, as shown in FIG. 1, detecting means 1 for detecting physical signals such as the brain wave, movement of the eyeballs and pulse wave, signal processing means 2 for processing the signal from the detecting means 1 and judging means 3 for judging the falling asleep by outputs from signal processing means 2.

In the conventional configurations, however, since they are constructed such that the detecting means 1 for detecting the brain wave, movement of eyeballs and pulse wave is installed directly on the scalp or skin of the body, such a problem was encountered that an inharmonious feeling due to the installation may disturb the sleeping.

2. Disclosure of the Invention

The present invention is designed to solve the above-mentioned problems, and therefore, it is an object thereof to provide a human monitoring apparatus which judges, first, whether there is the body on a bed or a seat so as not to make an erroneous detection as the body movement when things are placed on the bed or the sear, and detects sleep easily without installing and contacting the detecting means to the human body. By viewing the fact that movement of the body (hereinafter referred to as body movement) comes to a standstill on sleep, the human monitoring apparatus detects the body movement without contacting the body and detects the sleep in response to the quiescent time of the body movement.

In order to achieve the above-mentioned object, the present invention includes body movement detecting means which in turn includes at least one piezo-electric element disposed on a bed or a seat and detects movement of a human body on the bed or the seat. The body movement detecting means producing a signal. Also includes are absence judging means for judging the presence of a body on the bed or seat when the signal level is above the first set value and below a second predetermined set value, and body movement judging means for judging that the body has produced a rough body movement such as turning over on the bed or the seat when the signal level is above the second set value.

The present invention further includes a timer for resetting a time measurement whenever the absence or rough body movement is judged and starting the time measurement when the presence is judged, and sleep judging means for judging that the body has fallen asleep when a measured time of the timer exceeds a predetermined set time.

In the present invention, the body movement detecting means is constituted by, at least one piezo-electric element disposed on bedding or a seat, a filter which filters a certain specific frequency component with respect to respective signals of the piezo-electric element, an amplifier which amplifies the filter signal, a rectifier which rectifies the amplifier signal and a smoothing device which smoothes the rectifier signal.

The present invention is constituted by a piezo-electric element including of a high-molecular piezo-electric material such as polyvinylidene fluoride, which is processed into a thin film and bonded with a flexible electrode film on both surfaces thereof to form a tape.

In the present invention, the piezo-electric element is contained in a sheet shaped bag, and a stretchingly-and-shrinkingly movable stretch-shrink parts are provided on the end parts of the bag, and in addition, engaging and disengaging parts, which enable engaging and disengaging of end tip parts of the stretch-shrink parts from each other, are provided on respective ones of the end parts.

The present invention provides display means for displaying the signal level of the body movement detecting means, and first setting means capable of manually changing over between the first set value and the second set value, based on the signal level displayed by the display means.

The present invention comprises first memory means which samples and stores the signal level of the body movement detecting means at a predetermined period when the presence in,the bed or the seat is judged by the presence judging means, first operating means which operates a minimum value and a maximum value of the content stored in the first memory means, and second setting means which refreshes the minimum value as the first set value and the maximum value as the second set value.

The present invention comprises third setting means capable of setting the set time manually.

The present invention comprises second memory means for storing the measurement time of the timer whenever the time measurement of the timer is reset, second operation mans for operating a frequency distribution of the measurement time stored in the second memory means, third operating means which operates to obtain a time T in a manner that the ratio of the cumulative frequency until the time T is the frequency distribution against the total cumulative frequency shows a certain predetermined value, and fourth setting means which executes the storing and operating operation at every fixed period thereby to refresh the setting with the time T as the set time.

In the present invention, the body movement detecting means comprises at least one piezo-electric element disposed on bedding or a seat, a filter which filters a certain specific frequency component for respective signals of the piezo-electric element, a first amplifier which amplifies the filter signal, a second amplifier having a smaller amplification than the first amplifier for amplifying the filter signal, a first rectifier which rectifies the first amplifier signal, a second rectifier which rectifies the second amplifier signal, a first smoothing device which smoothes the first rectifier signal, and a second smoothing device which smoothes the second rectifier signal, and further comprises absence judging means for judging absence of the body on the bedding when the signal level of the first smoothing device is below the first set value, presence judging means for judging presence of the body on the bed or the seat in a quiet state when the signal level of the first smoothing device is above the first set value, and the signal level of the second smoothing device is below the third set value predetermined, and body movement judging means for judging the rough body movement of the body of the bed or the seat when the signal level of the second smoothing device is above the third set value.

In the present invention, the piezo-electric element is disposed on a toilet seat or a bath tub.

Furthermore, the present invention comprises the body movement detecting means for detecting a fine movement propagated by the function of heart and breathing of a human body on a bed or a seat, said body movement detecting means producing a signal, presence judging means for judging whether or not the human body is present on the bed or the seat in accordance with the signal of the body movement detecting means.

The present invention outputs a voltage signal generated by piezo-electric effects, when at least a piezo-electric element disposed on a bed or a seat is deformed by the body movement, after filtering, amplifying, rectifying and smoothing it in the smoothing device. The present invention judges by the absence judging means that the body is absent on the bed or the seat when the signal level of the body movement detecting means is below a predetermined first set value, judges by the presence judging means, that the body is on the bed or the seat in a quiet state when the said signal level is above the first set value and below the predetermined second set value, and judges by the body movement judging means that the body has moved roughly on the bed or the seat such as turning over when the signal level is above the second set value, whereby the timer resets time measurement whenever the absence is judged or the rough body movement is judged and starts the measurement when the present in the bed or the seat is judged, and when the measurement time of the timer exceeds a predetermined set time, the sleep judging means judges that the body has fallen asleep.

In the present invention, the above-mentioned piezo-electric element is constituted by processing a high-molecular piezo-electric material such as polyvinylidene fluoride into a thin film and bonding flexible electrode films on both faces thereof to form a tape.

Also, in the present invention, the piezo-electric element is contained in a sheet shaped bag, on the portions of said sheet-shaped bag, and a stretchingly-and-shrinkingly movable stretch-shrink parts are provided on the end parts of the bag, and in addition, engaging and disengaging parts, which enable engaging and disengaging of end tip parts of said stretch-shrink parts from each other, are provided on respective ones of said end parts.

The present invention displays the signal level of the body movement detecting means by display means, and is able to change the first set value and the second set value manually in response to the signal level.

In the present invention, when the presence in bed is judged by the presence judging means, the signal level of the body movement detecting means is sampled and stored at a period predetermined; and further a minimum value and a maximum value of the memory content are operated hence to refresh the minimum value as the first set value and the maximum value as the second set value by the second setting means.

The present invention is capable of setting the set time manually by the third setting means.

The present invention stores the measurement time of the timer and operates the frequency distribution of the measurement time, every time the time measurement of the timer is reset, operates the time T in a manner that the ratio of cumulative frequency until the time T in the frequency distribution to the total cumulative frequency show a predetermined certain value, and refresh the setting taking the time T as the set time.

The present invention filters a signal of, at least, one piezo-electric disposed on the bed or the seat, amplifies the filtered signal respectively by two amplifiers having different amplifications, and rectifies and smoothes them. Then, distinguishing vibration propagated to the piezo-electric element by movement of other in the vicinity of the bed or the seat, and vibration applied to the piezo-electric element by the body movement of a person in the bed or the seat, and judging the absence, presence and rough body movement.

The present invention judges whether or not the body is present on the toilet seat or a bath tub.

Furthermore, the present invention detects the presence of the body on the bed or the seat in accordance to the signal of the body movement detecting means which detects the fine movement propagated by the function of heart and breathing of the body.

BEST MODE FOR CARRYING OUT THE INVENTION

Figure 1:
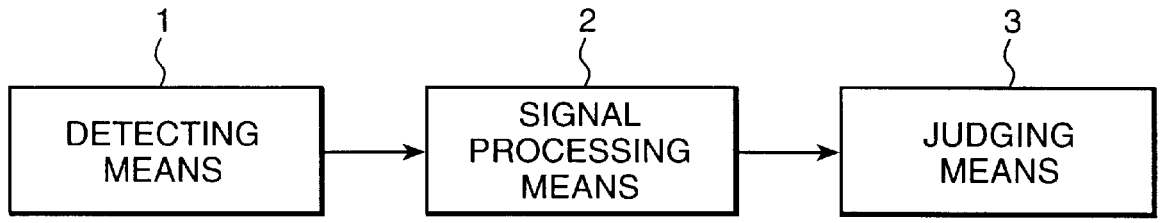
FIG. 1 is the block diagram of the conventional human monitoring apparatus.
Figure 2:
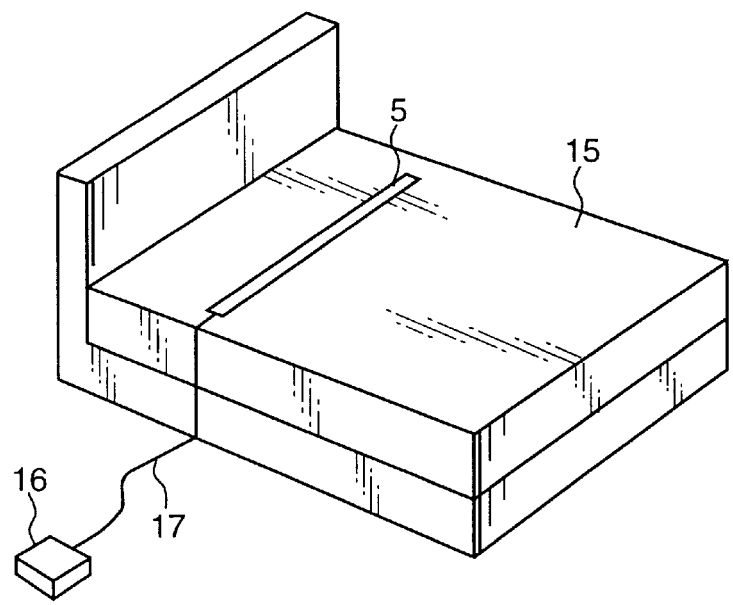
FIG. 2 is an external perspective view of a human monitoring apparatus in a first working example of the present invention.
Figure 3:
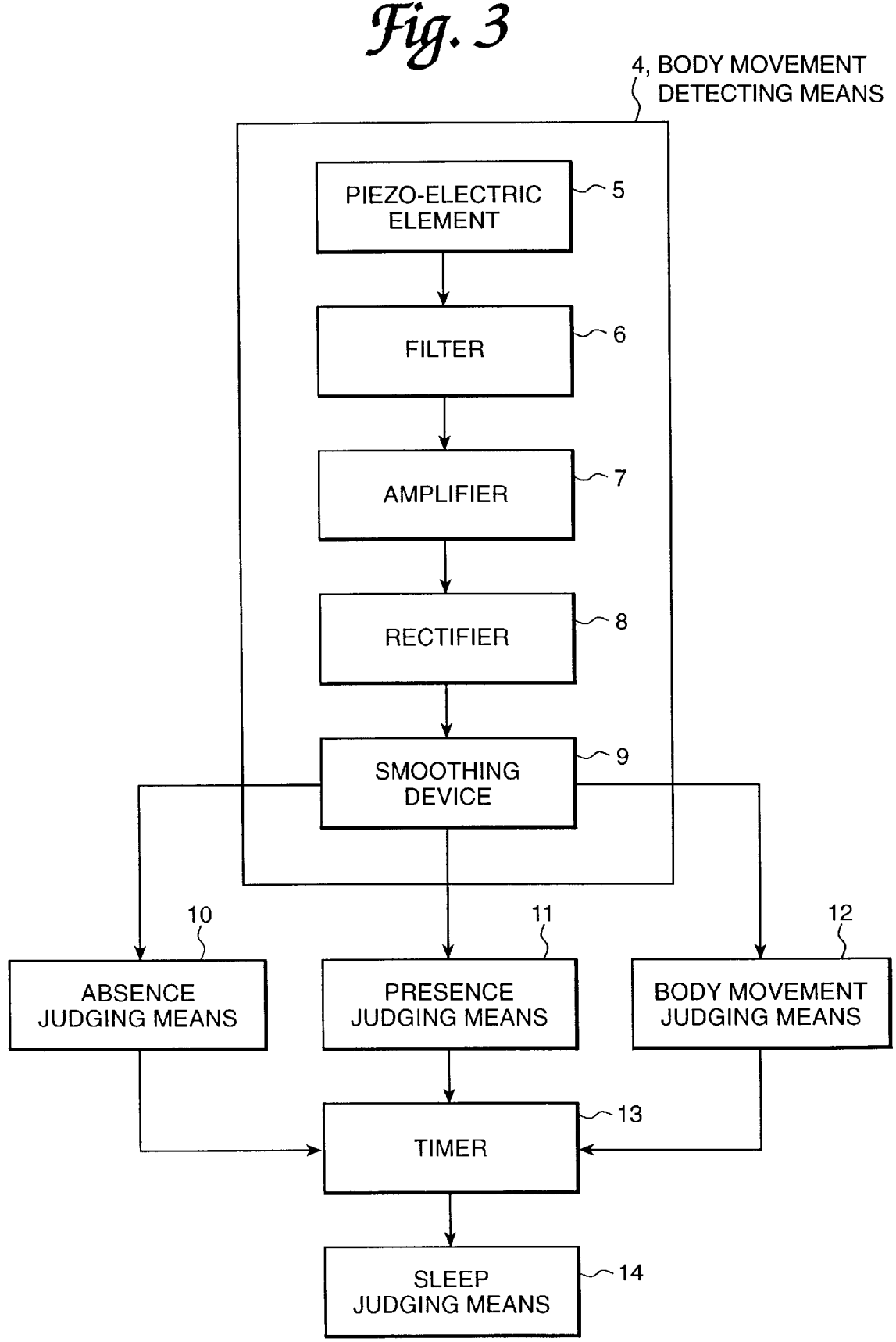
FIG. 3 is a block diagram showing a signal processing system of the apparatus.

In the following, a first working example of the present invention will be described with reference to the accompanying drawings. FIG. 2 is a perspective view when the working example is installed on a bed, and FIG. 3 is a block diagram. In FIG. 2 and FIG. 3, numeral 4 designates body movement detecting means consisting of a piezo-electric element 5, filter 6, amplifier 7, rectifier 8 and smoothing device 9. Numeral 10 designates absence judging means, numeral 11 designates presence judging means, numeral 12 designates body movement judging means, numeral 13 designates a timer and numeral 14 designates sleep judging means. The piezo-electric element 5 is constituted by a high-molecular material such as polyvinylidene fluoride which is processed into a thin film and bonded with a flexible electrode film on both surfaces thereof to form a tape, and is fixed on the surface of a mattress 15 as shown in FIG. 2. Numeral 16 designates a circuit unit wherein the filter 6, amplifier 7, rectifier 8, smoothing device 9, absence judging means 10, presence judging means 11, body movement judging means 12, timer 13 and sleep judging means 14 (none of which is shown in FIG. 2) are contained. The piezo-electric element 5 and the circuit unit 16 are connected with a shielded wire 17.

Figure 4A:
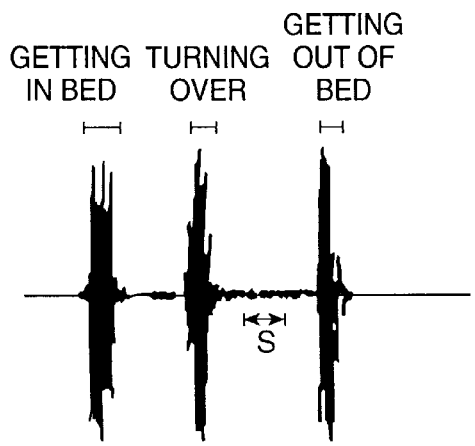
FIG. 4(a) is an output waveform diagram of a piezo-electric element of the apparatus.
Figure 4B:
FIG. 4(b) is an expanded output waveform diagram of a portion S of the piezo-electric element in FIG. 4(a).

According to the configuration of this working example, the present invention is operated as follows. In case the body is present on the bed, and when the piezo-electric element 5 is deformed by the fine and rough body movements of the body, voltage is produced from the piezo-electric element 5 responsive to a degree of deformation. Actual output signal from the piezo-electric element 5 is shown in FIG. 4(a) and FIG. 4(b). A large level signal of FIG. 4(a) is the case of rough body movement such as getting in and out from the bed and turning over. FIG. 4(b) shows an expanded waveform of a portion 5 in FIG. 4(a). When the body is in bed in a quiet state, a fine body movement propagated by the fine body movement or the functioning of heart and breathing is detected by the piezo-electric element 5 as shown in FIG. 4(b).

Figure 5:
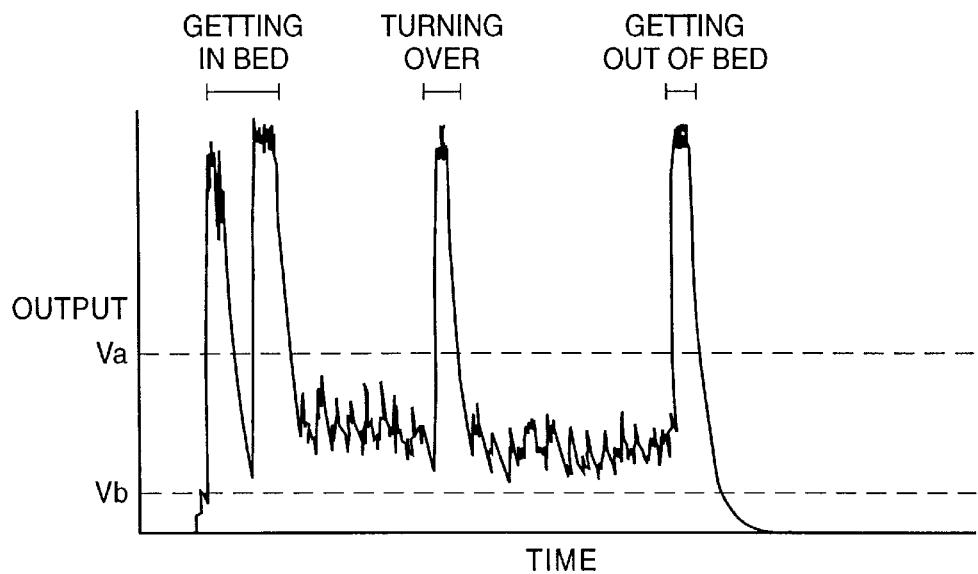
FIG. 5 is an output waveform diagram of a smoothing device of the apparatus.

About 1 to 10 Hz components of the output signal of the piezo-electric element 5 is filtered by the filter 6, and after being amplified by the amplifier 7, rectified by the rectifier 8 and smoothed by the smoothing device 9. FIG. 5 shows the actual output signal from the smoothing device 9. From the figure, a large signal is outputted when the rough body movement such as getting in and out from the bed and turning over has occurred, while in case of quiet state besides that, a low level signal is obtained by the fine body movements stated above. When the body is absent, the signal level is zero. Based upon this, the following judgments are conducted responsive to the signal levels of the smoothing device 9. That is, when the signal level of the smoothing device 9 is below 9 first set value ($V_b$ in FIG. 5) predetermined, it is judged by the absence judging means 10 that the body is absent on the bed. In case the signal level of the smoothing device 9 is above $V_b$ and below a second set value ($V_a$ in FIG. 5) predetermined, it is judged by the presence judging means 11 that the body is present on the bed in a quiet state. In case the signal level of the smoothing device 9 is above $V_a$, it is judged by the body movement judging means 12 that the body on the bed has moved roughly. $V_a$ and $V_b$ can be obtained by experiments on a person being tested.

Next, when the signal from the presence judging means 11 is outputted, the time measurement operation is started by the timer 13. However, this time measurement operation is reset by the signal from the absence judging means 10 or the body movement judging means 12. Then, in the sleep judging means 14, it is judged that the body on the bed has fallen asleep, when the measurement time measured by the timer 13 exceeds 9 set time $T_0$ predetermined.

Figure 6:
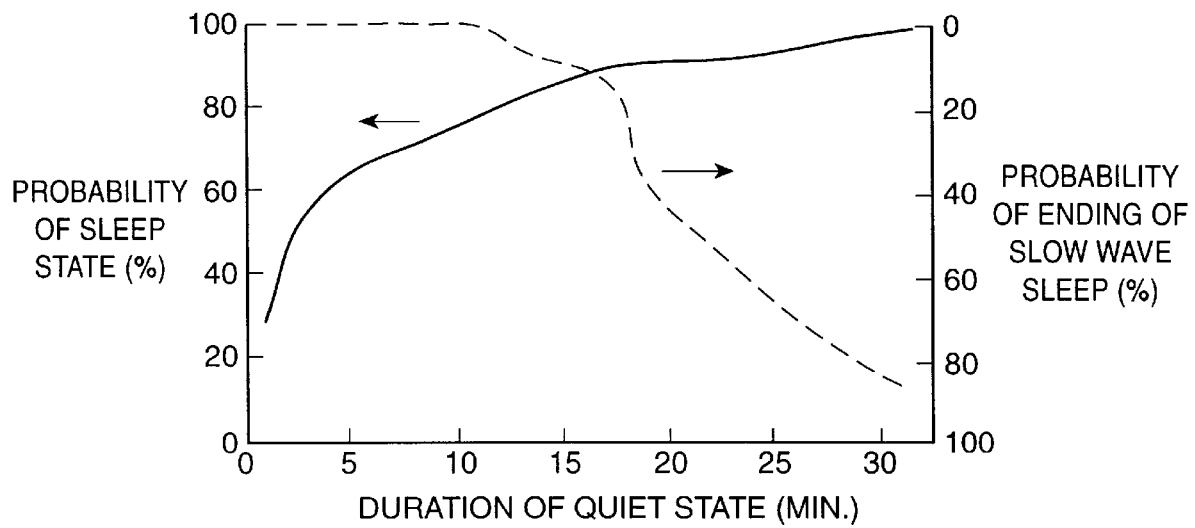
FIG. 6 is a characteristic diagram showing the relationship between a duration of quiet state and probability of the sleeping state.

With respect to deciding the set time $T_0$, we have made the following study on the relationship between the rough body movement and a sleeping state. That is, by knowing the fact that the rough body movement disappears on sleep, the relationship is obtained by experiments, between a duration of quiet state where there is no rough body movement and probability of sleep of a person in bed in that state. The result is shown in FIG. 6. In the figure, the duration of quiet state is plotted along the abscissa, and probability of sleep of the person who is tested against the duration of quite state is plotted along the left ordinate. In general, after a person falls asleep it moves to a slow wave sleep which is deep sleep, and after some time, the rough body movement takes place and the slow wave sleep comes to an end. From this fact, probability of occurrence of the rough body movement and completion of the slow wave sleep when the quiet state has continued for some time is plotted along the right side ordinate. From the figure, it is known that, for example, when the quiet state lasts for 15 minutes there is about 85% probability of sleep and 10% probability of end of the slow wave sleep, thus it is possible to judge sleep at a sufficient level for practical use by measuring the duration of quiet state. As the above-mentioned set time T12$_0$, 10 to 15 minutes are adequate.

Though the piezo-electric element is deformed to produce the voltage even when things are placed on the mattress, since there is no fine body movement due to the pulses and breathing of the body in a lifeless object as things, there is no occurrence of malfunction. That is, no matter who is in bed, it is possible to judge sleep as far as the fine body movement is detected. Even when the impact is exerted on the bed by some action such as bed making, such one is not detected as the rough body movement as far as the presence in bed is not judged.

By the above-mentioned operation, the body movement is detected by the piezo-electric element without contacting to the body, the presence in bed is judged by detecting the fine body movement of the body, and the sleep is judged from the duration of quiet state only at presence in bed, and accordingly no matter who is in bed the sleep is judged reliably as far as the fine body movement is judged. Also, even when the impact is exerted on the bed by some actions such as placing lifeless objects like things on the bed or making bed, it is not judged as the rough body movement as far as the presence in bed is not judged, and thus the sleep can be judged without error. Also, since the piezo-electric element has a flexible property and is formed into a tape, it can be disposed easily on the bed.

In the working example mentioned above, though the piezo-electric element is disposed on the mattress, it may be constructed to contain in the mattress or to dispose on the bed-frame, or further on a futon, sheet, pillow and so on, as far as they are within a range where the fine body movement can be detected.

Also, in the aforesaid working example, though one piezo-electric element was used to detect the body movement, it may be so constructed that plural piezo-electric elements are disposed on the bedding; thereby the body movement is detected by either of the piezo-electric elements even when tossing about on sleep or in case of an individual difference in height, so that accuracy of detecting the body movement is improved.

Figure 7:
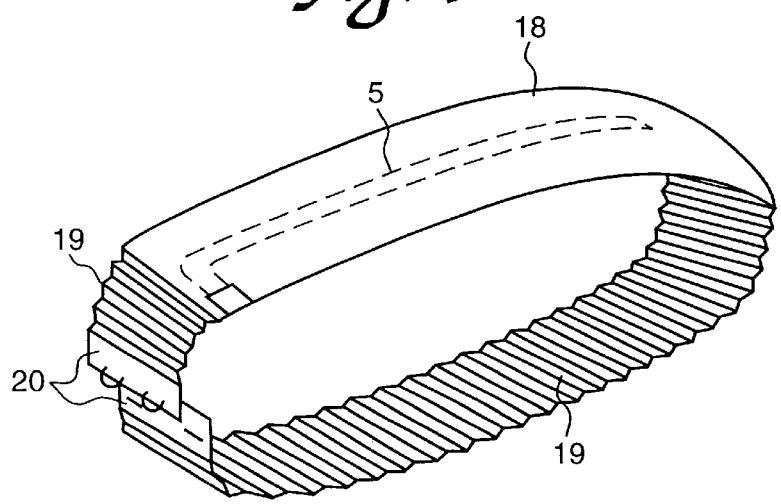
FIG. 7 is an external perspective view of body movement detecting means in a second working example of the present invention.

A second working example of the present invention will be explained in the following. This working example differs from the above-mentioned working example in a point that, as shown in FIG. 7, the piezo-electric element 5 is contained in a sheet bag 18, on the end portions of which stretchingly-and-shrinkingly movable stretch-shrink parts 19 are provided, and in addition, engaging-and-disengaging parts 20, which enable engaging-and-disengaging of end tip parts by hooks are provided respectively.

Figure 8:
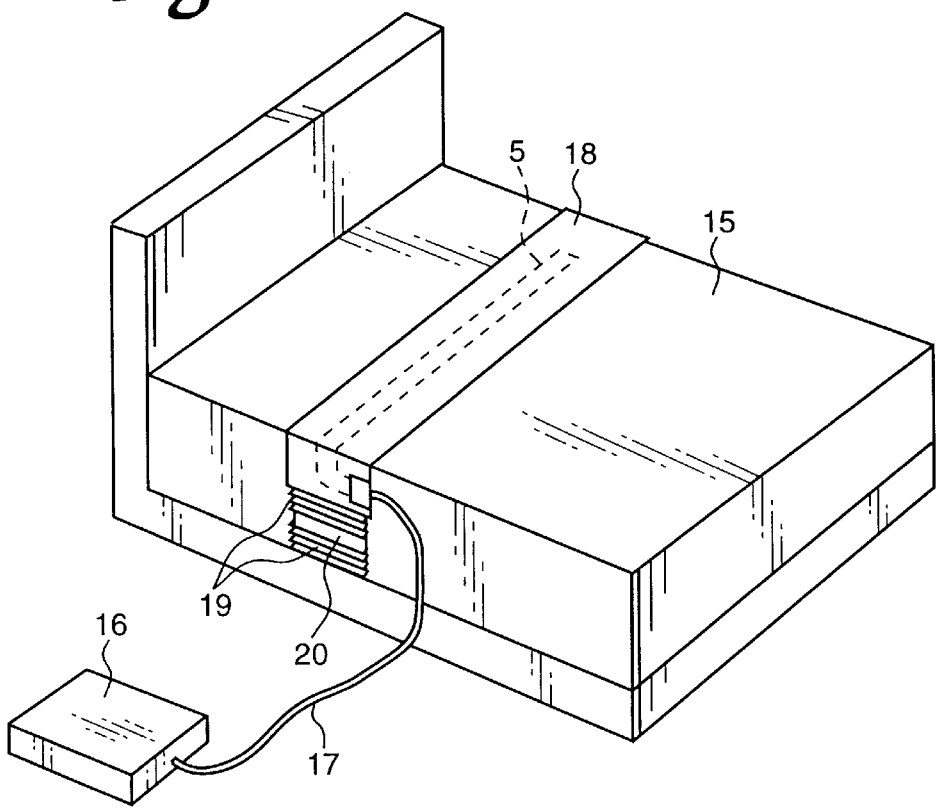
FIG. 8 is an external perspective view showing a state wherein the body movement detecting means is installed on bed.

By the configuration described above, it can be installed easily on any kind of beddings since the stretch-shrink parts 19 is provided. And example of installing the present working example on a bed is shown as one example in FIG. 8. It has an effect of protecting the piezo-electric element 5 from breaking even when the body moves violently on the bedding, since the impact is absorbed by the stretch-shrink parts 19. Furthermore, since the edges of the sheet 18 are removable, they can be easily fit on and removed from the bedding for washing.

Figure 9:
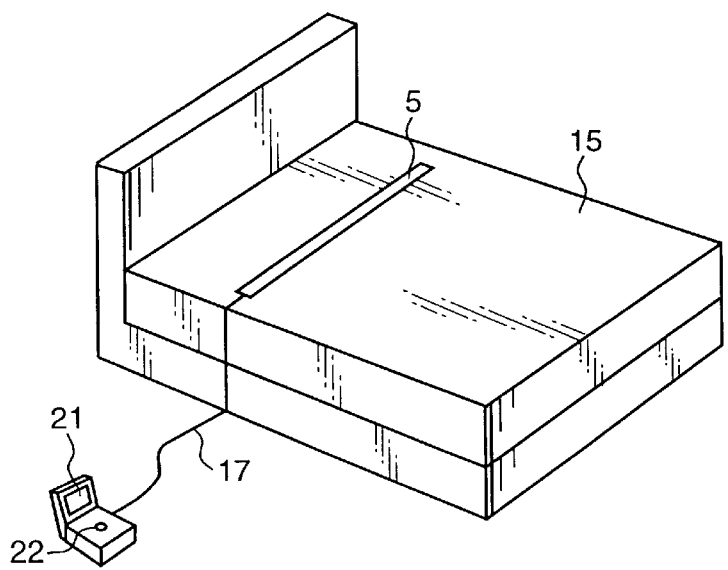
FIG. 9 is an external perspective view of a human monitoring apparatus in a third working example of the present invention.

A third working example of the present invention will be described in the following. Difference of this working example from the above-mentioned working example is in a point that, as shown in FIG. 9, display means 21 which displays the signal level of the smoothing device 9 and first setting means 22 which is capable of setting the $V_b$ and $V_a$ manually in response to the content displayed on the display means 21 are included.

By the above configuration, the user himself can set the $V_b$ and $V_a$ manually by the first setting means 22 in response to the signal level of the smoothing device 9 displayed on the display means 21. Accordingly, even when there is an individual difference in the magnitude of fine body movement, the user can select a threshold value which suits him, and therefore the fine body movement can be detected reliably to detect the presence of the body.

Figure 10:
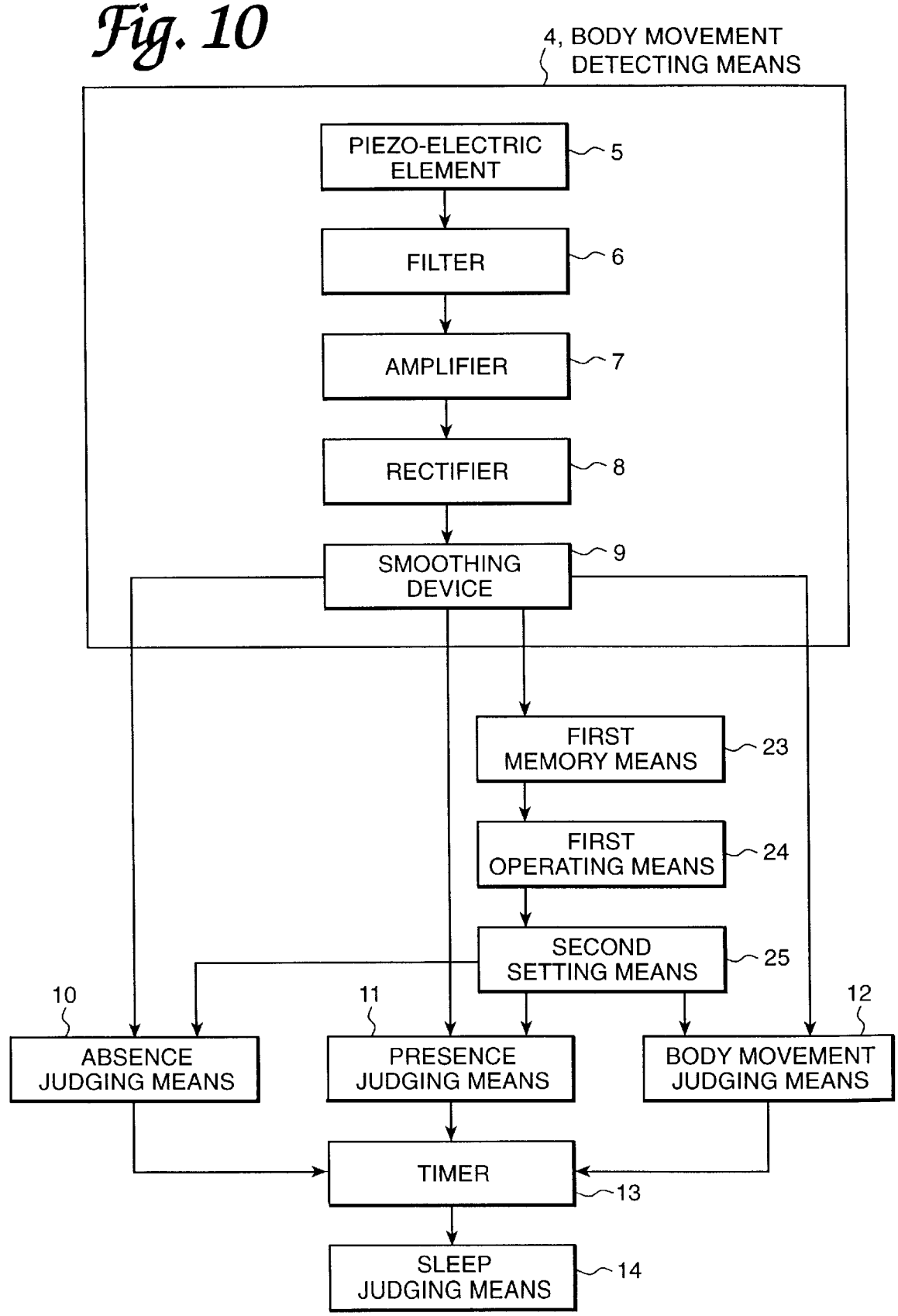
FIG. 10 is a block diagram showing a signal processing system of a human monitoring apparatus in a fourth working example of the present invention.

A fourth working example of the present invention will be described in the following. Difference of this working example from the above-mentioned working example is in a point that: as shown in FIG. 10, to include first memory means 23 for sampling and storing the signal level of the smoothing device 9 of the body movement detecting means 4 at a period predetermined when the presence in bed is judged by the presence judging means 11, first operating means 24 for operating a minimum value and a maximum value of the content stored in the first memory means 21, and second setting means 25 for refreshing the minimum value as the first set value $V_b$ and the maximum value as the second set value $V_a$ are included.

By the above-mentioned configuration, when the signal level of the smoothing device 9 is stored in the first memory means 23, the minimum value and the maximum value of the stored content are operated, and the minimum value and the maximum value are respectively represented as $V_b$ and $V_a$.

By the above-mentioned configuration, even when there are individual differences in the magnitude of fine body movements, since a set value for successively storing the magnitudes of fine body movement and detecting the fine movement is learned, the fine body movement can be detected reliably to detect the sleep.

Figure 11:
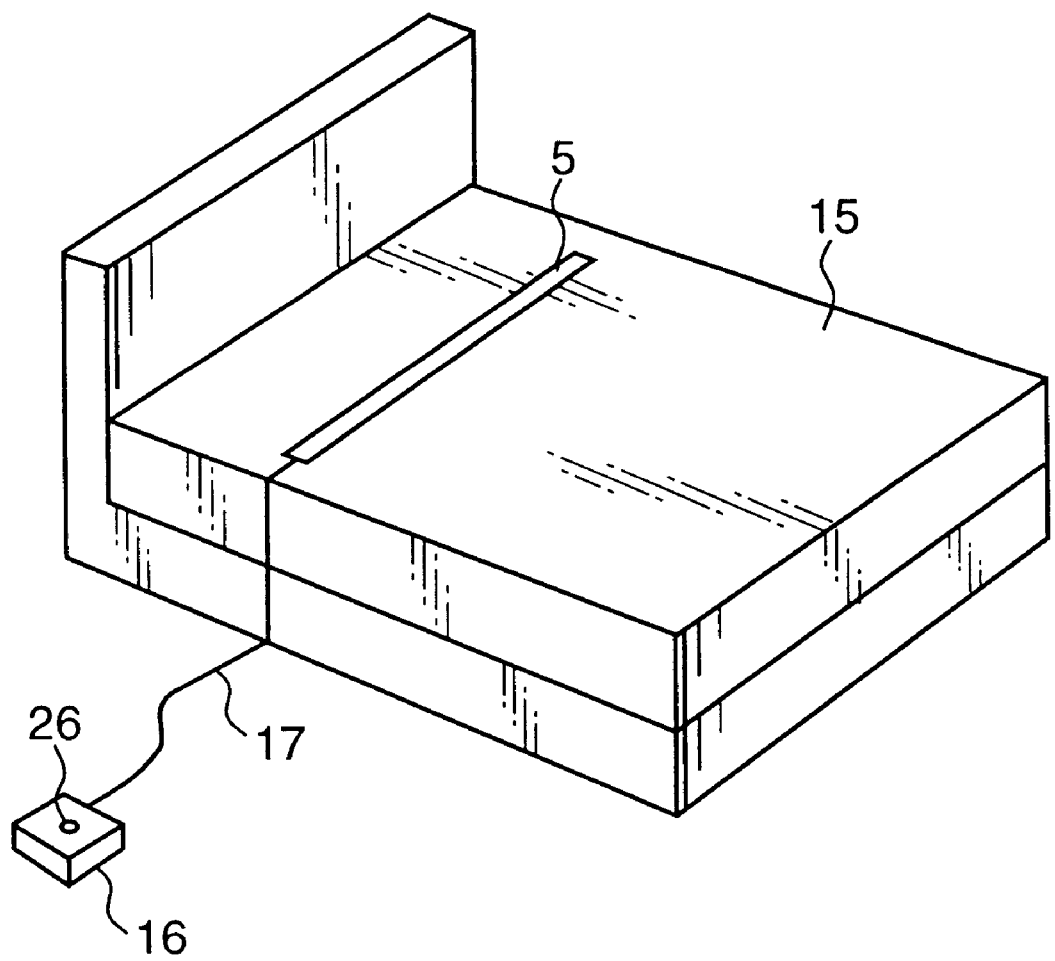
FIG. 11 is an external perspective view of a sleep detecting means in a fifth working example of the present invention.

A fifth working example of the present invention will be described in the following. Difference of this working example from the above-mentioned working example is in a point that, as shown FIG. 11, third setting means 26 capable of manually changing the set time $T_0$ which has been previously explained is provided. Thereby, even though there are individual differences in the duration of quiet state, the sleep can be detected reliably by selecting the set time $T_0$ which fits to himself by the user.

Figure 12:
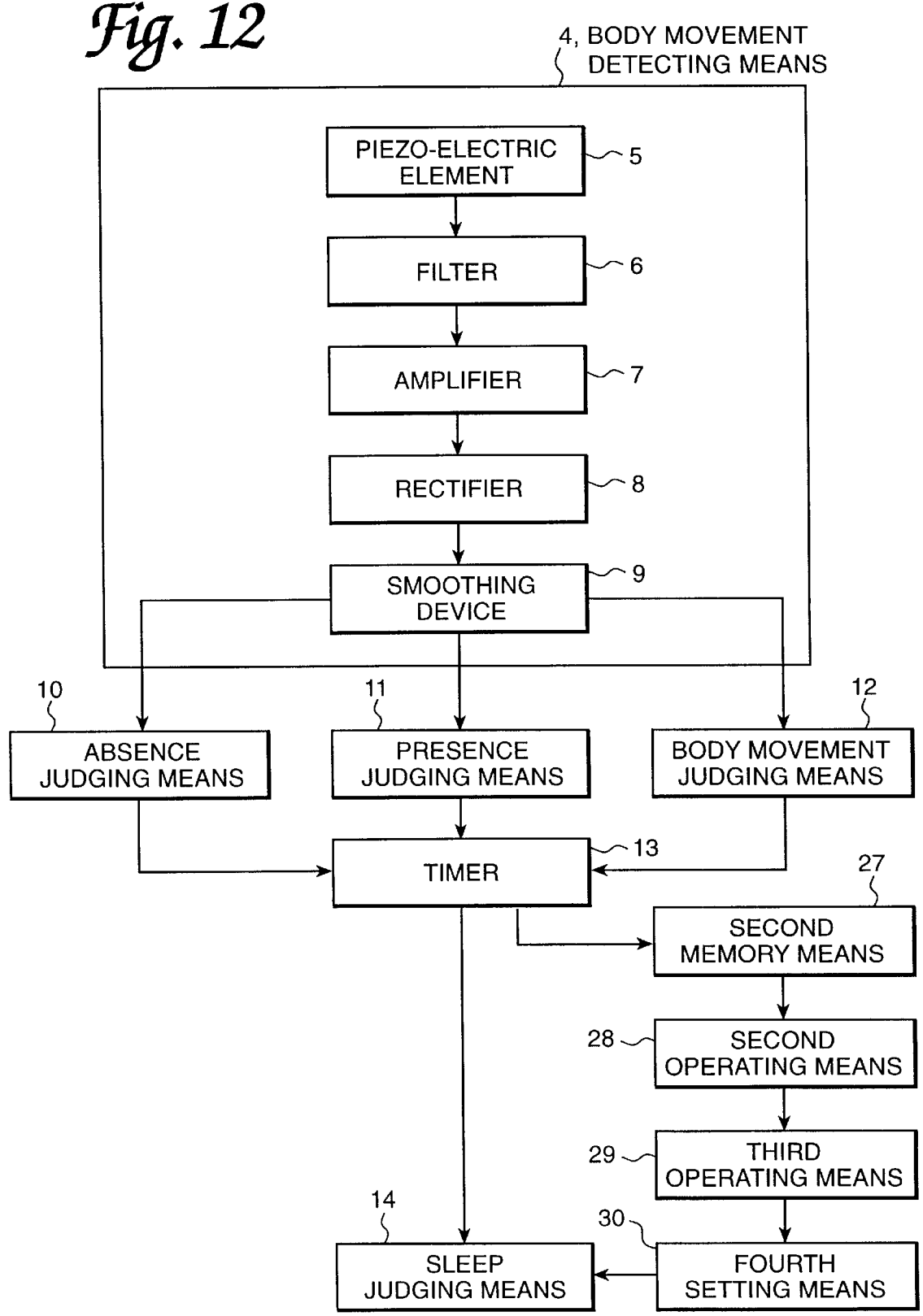
FIG. 12 is a block diagram showing a signal processing system of a human monitoring apparatus in a sixth working example of the present invention.

A sixth working example of the present invention will be described in the following. Difference of this working example from the above-mentioned working example is in a point that, as shown in FIG. 12, it comprises: second memory means 27 for storing the measurement time of the timer 13 every time the time measurement of the timer 13 is reset, second operating means 28 for operating an occurrence frequency distribution of the measurement time stored in the second memory means 28, third operating means 29 for operating to obtain a certain time T in a manner that a ratio of a cumulative frequency till the time T in the said occurrence frequency distribution to a total cumulative frequency shows a predetermined value, and fourth setting means 30 for conducting the storing and operating operations at every sixed period to refresh the setting with the time T as the set time $T_0$.

Figure 13:
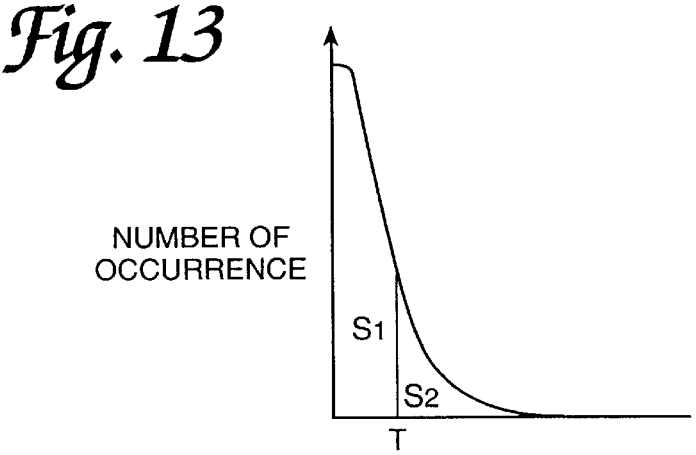
FIG. 13 is a characteristic diagram showing a frequency distribution of the body movement quiescent time.

By the above-mentioned configuration, the measurement time of the timer 13 is stored in the second memory means 27, every time the time measurement operation of the timer 13 is reset by the signal of the absence judging means 10 or body movement judging means 12. Then, the occurrence frequency distribution of the measurement time having been stored is operated by the second operating means 28. FIG. 13 shows the frequency distribution operated. In the figure, the abscissa is graduated by measurement time, and the ordinate is graduated by frequency. Next, in the occurrence frequency distribution, the time T is operated by the third operating means 29 in a manner that a ratio of a cumulative frequency till a certain time to a total cumulative frequency (S1/(S1+S2) in FIG. 13) shows a predetermined value $S_0$. Then, the time T is set by the fourth setting means 30 as the set time $T_0$. The value $S_0$ can be obtained by experiments on subject.

Thereby, even when there are individual differences in durations of quiet state the sleep can be detected reliably, since the duration of quiet state is successively stored and the set time for detecting the sleep is learned.

Figure 14:
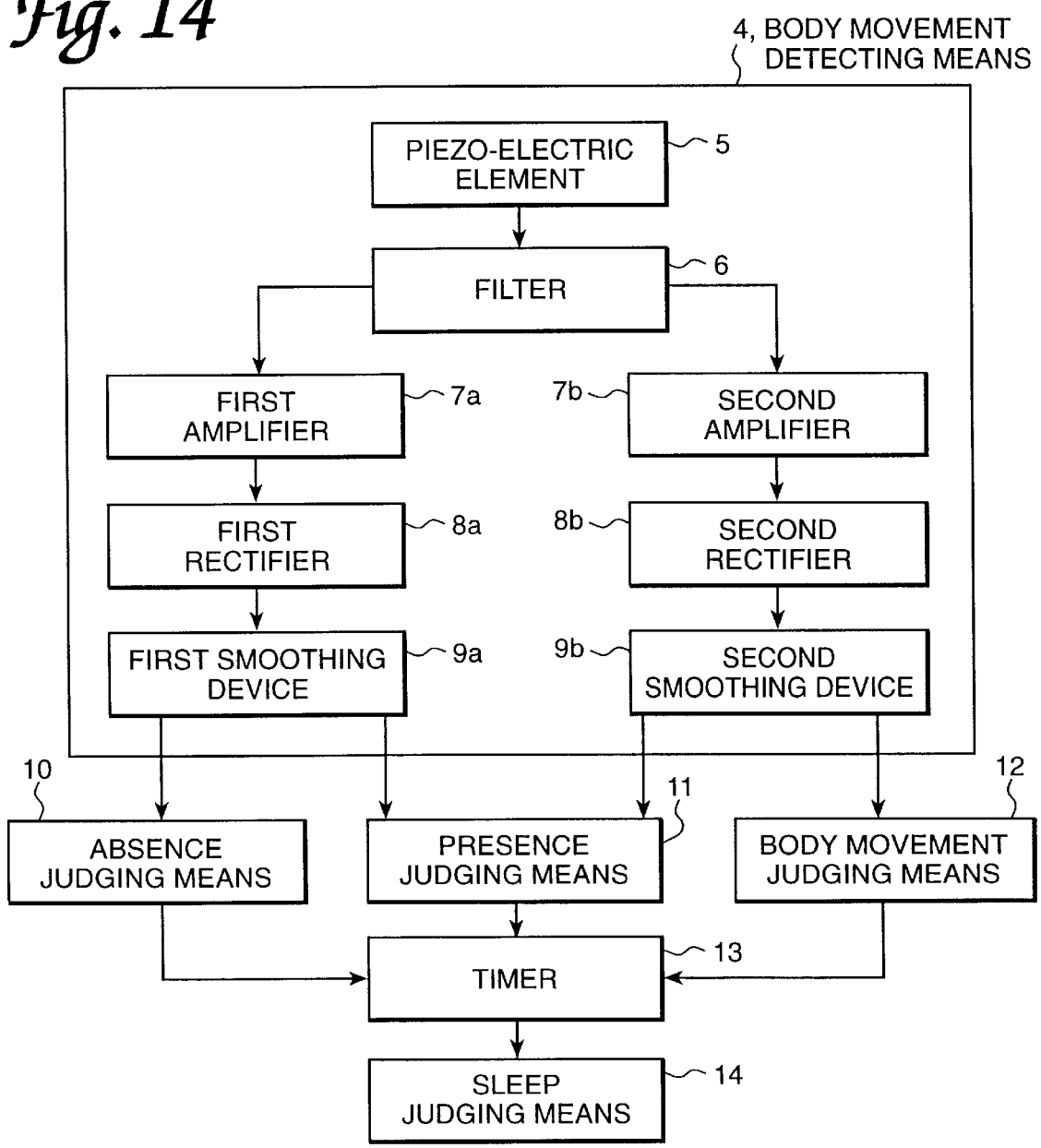
FIG. 14 is a block diagram of a human monitoring apparatus in a seventh working example of the present invention.

A seventh working example of the present invention will be described in the following. Difference of this working example from the above-mentioned working example is in a point that, as shown in FIG. 14, the body movement detecting means 4 comprises: at least one piezo-electric element 5 disposed on the bedding, a filter 6 which filters a certain specific frequency component for respective signals of the piezo-electric element 5, a first amplifier 7a which amplifies the signal from the filter 6, a second amplifier 7b which amplifies the signal from the filter 6, a second amplifier 7b having a smaller amplification than the first amplifier 7a and amplifying the signal from the filter 6, a first rectifier 8a, a second rectifier 8b, a first smoothing device 9a which smoothes the signal from the first rectifier 8a, and a second smoothing device 9b which smoothes the signal from the second rectifier 8b; whereby the absence judging means 10 judges the absence of body on the bedding when the signal level of the first smoothing device 9a is below the first set value $V_b$, the presence judging means 11 judges the presence of body on the bedding in a quiet state when the signal level of the first smoothing device 9a is above $V_b$ and the signal level of the second smoothing device $9_b$ is below a third set value $V_c$ predetermined, and the body movement judging means 12 judges the rough body movement of the body on the bedding when the signal level of the second smoothing device 9b is above $V_c$.

Figure 15A:
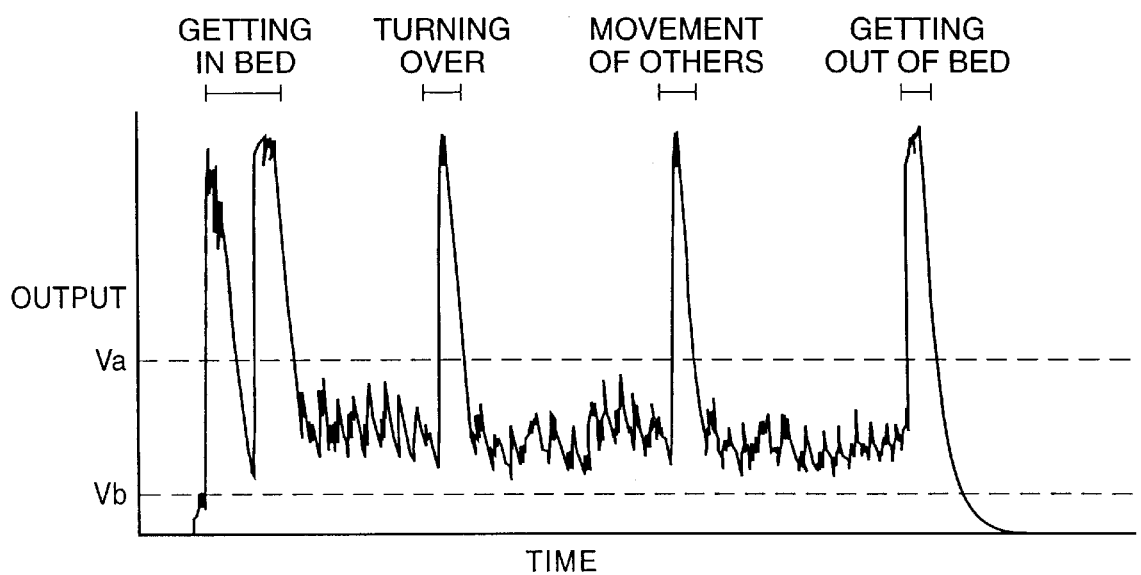
FIG. 15(a) is an output waveform diagram of a first smoothing device of the apparatus.
Figure 15B:
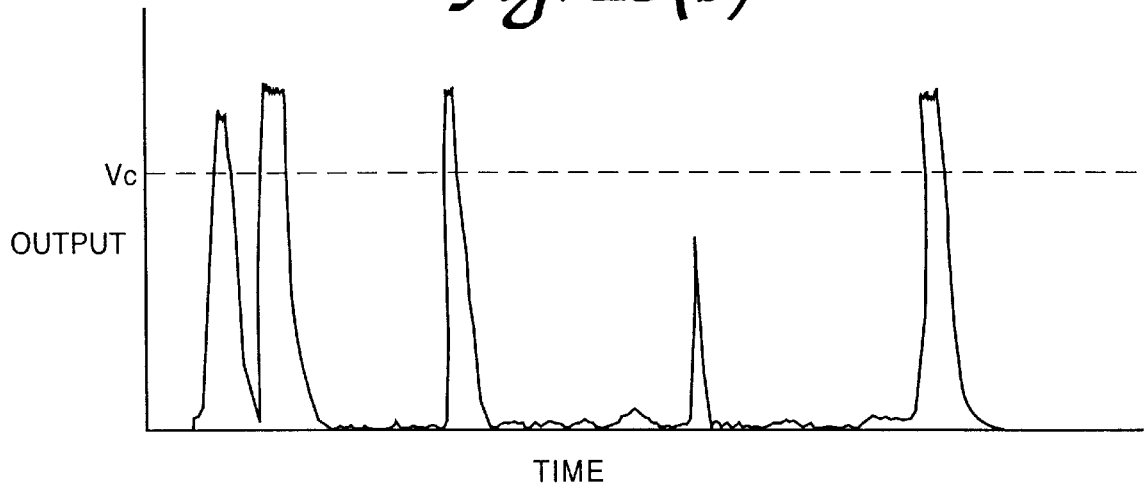
FIG. 15(b) is an output waveform diagram of a second smoothing device of the apparatus.

According to the configuration of this working example, the present invention operates as follows. In case the body is present on the bedding and when the piezo-electric element 5 disposed on the bedding is deformed by the fine or rough movement of the body, a voltage is produced from the piezo-electric element 5 responsive to a degree of deformation. This output signal is filtered by the filter 6 and the signal is amplified by the first amplifier 7a, recited by the first rectifier 8a and smoothed by the first smoothing device 9a, and further amplified by the second amplifier 7b, rectified by the second rectifier 8b and smoothed by the second smoothing device 9b. Here, the first amplifier 7a has a same characteristic as the amplifier 7 of the conventional example previously described, and the second amplifier 7b has the amplification set smaller than that of the first amplifier 7a. And, the two smoothing devices respectively have the same characteristics as the rectifier and integrator of the conventional examples previously described. FIG. 15(a) shows a signal waveform of the first smoothing device 9a, and FIG. 15(b) shows a signal waveform of the second smoothing device 9b. Here, though the magnitude of deformation applied to the piezo-electric element 5 by both the rough body movement of the body in bed and movement of other is naturally larger in the former, since the first amplifier 7a has as same high amplifying characteristic as the amplifier in the conventional example previously described as shown in FIG. 15(a), the signal level by the rough body movement such as getting in and out of the bed and turning over and the signal level by movement of other are both above the first set value $V_a$ described before; and the rough movement of the body in bed and the movement of other an not be distinguished. However, since the amplification of the second amplifier 7b is set smaller than that of the first amplifier 7a, the signal level of the movement of other is smaller as compared with the rough body movement of the person in bed as shown in FIG. 15(b); and thus when the third set value $V_c$ is set as shown in the figure, it is possible to distinguish the rough body movement of the person himself in bed and the movement of other.

Thereby, the following judgments are made responsive to the signal levels of the first smoothing device 92 and the second smoothing device 9b. In case the signal level of the first smoothing device 9a is below $V_b$, it is judged by the absence judging means 10 that the body is absent on the bedding. In case the signal level of the first smoothing device 9a is above $V_b$ and the signal level of the second smoothing device 9b is below $V_c$, it is judged by the body movement judging means 12 that the body on the bedding has produced rough body movement. Next, when the signal is outputted from the presence judging means 11, the time measurement operation is started by the timer 13. However, the time measurement operation is reset by the signal of the absence judging means 10 or the body movement judging means 12. And, in the sleep judging means 14, when the measurement time measured by the timer 13 exceeds the set time $T_0$ described before, it is judged that the body has fallen asleep on the bedding.

By the above-mentioned operation, according to this working example, by adding an amplifier having a smaller amplification than the conventional example in signal processing circuit of the sleep judgment of the conventional example, the vibration propagation by the body movement of the person in bed and movement of other can be distinguished, thus it is possible to provide a sleep detecting apparatus without malfunction in judging the sleep.

In the above working examples, though the piezo-electric element was disposed on the bedding, the detection may be made by a construction that the piezo-electric element is disposed on a seat or furniture such as a sofa and a study chair to detect the presence or the sleep. Also, the piezo-electric element may be disposed on a toilet seat or a bath tub to detect the presence or the sleep.

While the working example of the present invention has been described above, as fields of application of the present invention there are so many besides aforementioned; for example, it may be applied widely and used practically as a control signal of an air conditioner, lightings and video and audio equipment for realizing a comfortable sleeping environment, or used as measuring instruments for sleeping experiments in clinical field such as a medical treatment of insomnia, or used as monitoring equipment for sleeping management and bed management in hospital and at-home case.

INDUSTRIAL APPLICABILITY

As described hereinabove, according to a human monitoring apparatus of the present invention, the following effects can be obtained.

The body movement is detected without contacting to the human body by the piezo-electric element, the fine body movement is detected to judge the presence in a bed, or a seat and sleep is judged from the duration of quiet time only in case of the presence in the bed, or the seat, and therefore the sleep is judged no matter who is in the bed or the seat as far as the fine body movement is detected. And even when the impact is exerted on the bed or the seat by some action such as placing a lifeless object like things or bed making, it is not detected as the rough body movement as far as the presence in the bed or the seat is not judged, and thus it is possible to judge the sleep without malfunction. Therefore it is possible to detect the sleep easily without installing detecting means for detecting a brain wave, movement of eyeballs and pulse wave on the human body, and without contacting thereto as in the past.

Also, since the piezo-electric element has a flexible property and is formed into a tape, it can be easily disposed on the bedding or a seat.

Besides, the piezo-electric element is contained in a sheet bag, on the respective end portions of which stretchingly-and-shrinkingly movable stretch-shrink parts are provided, and besides, engaging-and-disengaging parts, which enable engaging-and-disengaging of the end tip parts are provided, and therefore it can be installed easily on any beddings, and the piezo-electric element can be prevented from breaking, since the impact is absorbed by the expansion even when the body moves violently on the bedding.

Since setting means whereby the user can set a set value for optionally detecting the body movement is provided taking into account of an individual difference in the magnitude of body movement, the body movement can be detected more reliably to detect the presence of the body.

Moreover, since the magnitude of body movement is successively stored and a set value for detecting the body movement is obtained by the learning, taking into account of an individual difference in the magnitude of body movement, it is possible to detect the body movement more reliably to detect the presence of the body.

Also, since setting means whereby the user can set a set time value of the body movement quiescent time optionally is provided, taking into account of an individual difference in the quiescent time of the body movement, it is is possible to detect the sleep more reliably.

Moreover, since a frequency distribution of the body movement quiescent time is operated to obtain a set time value of the body movement quiescent time, taking into account of an individual difference in the quiescent time of the body movement, the sleep can be detected more reliably.

Furthermore, by adding an amplifier having a smaller amplification than the conventional example in a signal processing circuit of the sleep judgment, it is possible to distinguish vibration propagations by the body movement of the person in bed and the action by others, thus a sleep detecting apparatus without malfunction in judging the sleep can be provided.

What is claimed is:

1. Human monitoring apparatus comprising:

body movement detecting means which includes at least one piezo-electric element disposed on a surface supporting a body and that detects a rough body movement of the body on the surface, the rough body movement being a movement whereby the position of the body on the surface is substantially altered, and a fine movement of the body on the surface, the fine body movement being movement associated with one of heartbeat and respiration, the body movement detecting means producing a signal that is proportional to an amount of the movement of the body;

absence judging means for judging that there is no fine body movement and no rough body movement indicative of an absence of the body on the surface responsive to the signal of the body movement detecting means being below a first value;

presence judging means for judging a presence of the body on the surface by detecting the fine body movement, which is accomplished by determining that the signal of the body movement detecting means is above the first set value and below a second value;

body movement judging means for judging that the body has produced the rough body movement responsive to the signal of the body movement detecting means being above the second value;

a timer for resetting a time measurement responsive to the absence of the fine body movement being detected and for starting the time measurement responsive to the presence of the fine body movement being detected; and sleep judging means for judging that the body is asleep responsive to a measured time of the timer exceeding a predetermined time.

2. Human monitoring apparatus comprising:

a piezo-electric element disposed on a surface supporting a body and that detects a rough body movement of the body on the surface, the rough body movement being a movement whereby the position of the body on the surface is substantially altered, and a fine movement of the body on the surface, the fine body movement being movement associated with one of heartbeat and respiration, the piezo-electric element producing a signal that is proportional to an amount of the movement of the body;

a processing unit receiving the signal produced by the piezo-electric element and determining (1) that there is no fine body movement and no rough body movement, which indicates of an absence of the body on the surface responsive to the signal of the piezo-electric element being below a first value, (2) a presence of the body on the surface by detecting the fine body movement, which is accomplished by determining that the signal of the piezo-electric element is above the first set value and below a second value, and (3) that the body has produced the rough body movement responsive to the signal of the piezo-electric element being above the second value; and a timer for resetting a time measurement responsive to the absence of the fine body movement being detected and for starting the time measurement responsive to the presence of the fine body movement being detected, wherein the processing unit also judges that the body is asleep responsive to a measured time of the timer exceeding a predetermined time.

3. Human monitoring apparatus comprising:

body movement detecting means which includes at least one piezo-electric element disposed on a surface supporting a body and that detects a rough body movement of the body on the surface, the rough body movement being a movement whereby the position of the body on the surface is substantially altered, and a fine movement of the body on the surface, the fine body movement being movement associated with one of heartbeat and respiration, the body movement detecting means producing a signal that is proportional to an amount of the movement of the body;

absence judging means for judging that there is no fine body movement and no rough body movement indicative of an absence of the body on the surface responsive to the signal of the body movement detecting means being below a first value;

presence judging means for judging a presence of the body on the surface by detecting the fine body movement, which is accomplished by determining that the signal of the body movement detecting means is above the first set value and below a second value;

body movement judging means for judging that the body has produced the rough body movement responsive to the signal of the body movement detecting means being above the second value;

a timer for resetting a time measurement responsive to the signal from the absence judging means or the body movement judging means and for starting the time measurement responsive to the signal from the presence judging means, and sleep judging means for judging that the body is asleep responsive to a measured time of the timer exceeding a predetermined time.

4. Human monitoring apparatus comprising:

a piezo-electric element disposed on a surface supporting a body and that detects a rough body movement of the body on the surface, the rough body movement being a movement whereby the position of the body on the surface is substantially altered, and a fine movement of the body on the surface, the fine body movement being movement associated with one of heartbeat and respiration, the piezo-electric element producing a signal that is proportional to an amount of the movement of the body;

a processing unit receiving the signal produced by the piezo-electric element and determining (1) that there is no fine body movement and no rough body movement, which indicates an absence of the body on the surface responsive to the signal of the piezo-electric element being below a first value, (2) a presence of the body on the surface by detecting the fine body movement, which is accomplished by determining that the signal of the piezo-electric element is above the first set value and below a second value, and (3) that the body has produced the rough body movement responsive to the signal of the piezo-electric element being above the second value; and a timer for resetting a time measurement responsive to the absence of the body being detected or the rough body movement being detected and for starting the time measurement responsive to the presence of the body being detected.

* * * * *